United States Patent [19]

Schoenewaldt et al.

[11] 4,093,657

[45] June 6, 1978

[54] PROCESS FOR PREPARING MONOMER OF BILE ACID SEQUESTRANT POLYMER

[75] Inventors: Erwin F. Schoenewaldt, Watchung; Paul Sohar, Warren, both of N.J.

[73] Assignee: Merck & Co., Inc., Rahway, N.J.

[21] Appl. No.: 675,375

[22] Filed: Apr. 9, 1976

[51] Int. Cl.$^2$ ............................................... C07C 85/04
[52] U.S. Cl. ........................ 260/567.6 M; 260/583 R
[58] Field of Search ................. 260/567.6 M, 567.6 P

[56] References Cited

U.S. PATENT DOCUMENTS

| | | | |
|---|---|---|---|
| 3,068,235 | 12/1962 | Shapiro et al. | 260/567.6 M |
| 3,755,334 | 8/1973 | Sommer | 260/567.6 M |

FOREIGN PATENT DOCUMENTS

| | | | |
|---|---|---|---|
| 1,167,440 | 4/1954 | France | 260/567.6 M |

OTHER PUBLICATIONS

Gurin et al., J. Org. Chem., vol. 12, pp. 606–611 (1947).

*Primary Examiner*—James O. Thomas, Jr.
*Assistant Examiner*—James H. Reamer
*Attorney, Agent, or Firm*—Henry H. Bassford, Jr.; J. Jerome Behan; Rudolph J. Anderson, Jr.

[57] ABSTRACT

The invention disclosed herein relates to a novel process for preparing the monomer, 3-[N-(3-chloropropyl)-methylamino]-N,N,N-trimethyl-propan-1-aminium chloride, which comprises reacting N,N-bis(3-chloropropyl)methylamine with trimethylamine. The 3,3-ionene monomer thus obtained is a key intermediate for making the linear, unbranched, non-cross-linked polymer, poly-[{methyl-(3-trimethylammoniopropyl)imino}trimethylene dichloride], which is valuable as an oral bile acid sequestrant.

3 Claims, No Drawings

PROCESS FOR PREPARING MONOMER OF BILE ACID SEQUESTRANT POLYMER

DISCLOSURE OF THE INVENTION

This invention is concerned generally with improved methods for the preparation of 3-[N-(3-chloropropyl)-methylamino]-N,N,N-trimethyl-propan-1-aminium chloride, having the formula:

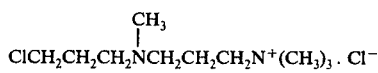

This compound, when heated in an oxygen-excluding environment, is converted to poly-[{methyl-(3-trimethylammoniopropyl)imino}trimethylene chloride]. This polymer is highly effective as an oral bile acid sequestrant.

The hydrochloride of 3-[N-(3-chloropropyl)methylamino]-N,N,N-trimethyl-propan-1-aminium chloride has been prepared by reacting thionyl chloride with 3-[N-(3-hydroxypropyl)methylamino]-N,N,N-trimethylpropan-1-aminium chloride hydrochloride. This 3-[N-(3-hydroxypropyl)methylamino]-N,N,N-trimethylpropan-1-aminium chloride hydrochloride has been prepared (a) by heating N,N,N-trimethyl-[3-(methylamino)]-1-propanaminium bromide with oxetane, and treating the resulting product with concentrated hydrochloric acid; and (b) by reacting 3-[N'-formyl-N'-(3-hydroxypropyl)amino]-1-propanamine hydrochloride with iodomethane in the presence of sodium carbonate to form 3-[N'-formyl-N'-(3-hydroxypropyl)amino]N,N,N-trimethyl-propan-1-aminium chloride, and reacting the latter with formalin in formic acid followed by concentrated hydrochloric acid.

In accordance with the present invention, N,N-bis(3-chloropropyl)methylamine hydrochloride is reacted with a base, as for example an alkali metal carbonate such as sodium carbonate, thereby forming the free tertiary amine, N,N,-bis(3-chloropropyl) methylamine, and this tertiary amine is reacted with trimethylamine to form a mixture of the diquaternary salt, bis(3-trimethylammoniopropyl) methylamine dichloride, and the desired monoquaternary salt, 3-[N-(3-chloropropyl)methylamino]-N,N,N-trimethylpropan-1-aminium chloride; this monoquaternary salt is converted to the corresponding 3-[N-(3-chloropropyl) methylamino]-N,N,N-trimethyl-propan-1-aminium chloride hydrochloride by reaction with hydrochloric acid.

The reaction between the N,N-bis(3-chloropropyl) methylamine hydrochloride and the alkali metal carbonate is conveniently carried out by bringing the reactants together in aqueous solution in the presence of a water-immiscible solvent such as ether, and vigorously agitating the mixture at about room temperature for a period of about 5-10 minutes, thereby completing the neutralization reaction; the tertiary amine base thus formed dissolves in the non-aqueous layer. The latter is separated from the aqueous layer, dried, and the solvent evaporated to give the free base, N,N-bis(3-chloropropyl)methylamine, in the form of an oil.

The reaction between the N,N,-bis(3-chloropropyl)-methylamine and the trimethylamine is conveniently conducted by allowing equimolar quantities of the reactants to stand in a polar organic solvent, preferably acetonitrile, for a period of about twenty hours during which time a white solid crystallizes; the reaction mixture is stirred for an additional 5–10 hour-period to complete crystallization of the by-product diquaternary salt, bis(3-trimethylammoniopropyl)methylamine dichloride, which is separated from the reaction mixture.

The resulting acetonitrile solution is evaporated in vacuo, the residual crystalline material is triturated with an organic solvent, such as ether, and the crystalline material is recovered to give the monoquaternary salt, 3-[N-(3-chloropropyl)methylamino]-N,N,N-trimethyl-propan-1-aminium chloride. The latter is ordinarily converted to the hydrochloride by dissolving the 3-[N-(3-chloropropyl) methylamino]-N,N,N-trimethyl-propan-1-aminium chloride in isopropanol, adding concentrated aqueous hydrochloric acid to the resulting solution, allowing the resulting mixture to stand at room temperature until crystallization is substantially complete, and recovering the crystalline material which is washed with an organic solvent such as isopropanol to give substantially pure 3-[N-(3-chloropropyl)methylamino]-N,N,N-trimethyl-propan-1-aminium chloride hydrochloride.

The latter compound is reacted with one equivalent of approximately 6.0N aqueous sodium hydroxide; the pH of the resulting mixture is adjusted to 11.9 by the addition of 1 N aqueous hydrochloric acid; the solution is separated from the precipitated sodium chloride by centrifugation; and the solution is heated at 100° C., with stirring under a nitrogen atmosphere, for a period of 18 hours. The reaction mixture is diluted with about 20 volumes of water, and subjected to ultrafiltration at 60 psi until the chloride content of the ultrafiltrate is negligible. The retentate is evaporated under reduced pressure, and the residual material is dried to give poly[{methyl-(3-trimethylammoniopropyl) imino}•trimethylene dichloride], which is highly effective as a bile acid sequestrant.

Experimental details for preparing the N,N-bis (3-chloropropyl)methylamine hydrochloride, used as starting material in the presentiy invented process for synthesizing 3-[N-(3-chloropropyl)methylamino]-N,N,N-trimethyl-propan-1-aminium chloride and its hydrochloride, are set forth hereinbelow and designated Preparations 1 and 2.

PREPARATION 1

An aqueous solution, prepared by mixing 448 grams of a 37.4% aqueous solution of methylamine and 249.5 grams of 3-chloro-1-propanol of 92% purity, is heated, with vigorous agitation in a glass-lined pressure vessel, at a temperature of 100° C. for a period of 3 hours. The brown-colored reaction solution thus obtained is cooled, about 195 grams of a 50% aqueous solution of sodium hydroxide is added, and the resulting solution is evaporated in vacuo until 200 ml of water has distilled (thereby removing excess methylamine) to produce an aqueous solution containing N-(3-hydroxypropyl)methylamine.

To this aqueous N-(3-hydroxypropyl)methylamine solution is added a second 249.5 g portion of 3-chloro-1-propanol, and the resulting mixture is heated under reflux at a temperature of approximately 105° C. for a period of about 5 hours, during which time about 195 grams of a 50% aqueous sodium hydroxide solution is added slowly at a rate sufficient to maintain the pH between about 8 and 9. The reaction mixture is cooled to room temperature, filtered, and the filtered aqueous solution is extracted with three 500 ml-portions of n- butanol. The butanol extracts are combined, evaporated to a small volume in vacuo, and the residual slurry is triturated with 300 ml of ethyl ether. The resulting ethereal slurry is filtered, thereby removing insoluble inorganic solid material, and the latter is washed with 100 ml of ethyl ether. The ether solution and washings are combined, the ether is evaporated therefrom in vacuo, and the residual oil is distilled in vacuo to give about 123 grams of N,N-bis(3-hydroxypropyl)methylamine; b.p. 110° C. at 150 microns pressure.

PREPARATION 2

A solution of about 60 grams of N,N-bis(3-hydroxypropyl)methylamine in 110 ml of chloroform is saturated, with cooling and stirring, with anhydrous hydrogen chloride gas. To the resulting two-phase liquid mixture is added, over a period of about 30 minutes at a temperature of 0–5° C., approximately 66 ml of thionyl chloride. The homogeneous solution thus obtained is allowed to stand at room temperature for a period of about 15 hours, the solution is then heated at reflux temperature for an additional two-hour period, and the chloroform is evaporated in vacuo from the light brown-colored reaction solution. The residual material is washed with ethanol, and is then crystallized from a mixture of 200 ml ethanol: 800 ml ether. The white crystalline product thus obtained is recovered by filtration, washed with three portions of ether, then with hexane, and dried in vacuo at 25° C. to give about 80 grams of N,N-bis(3-chloropropyl) methylamine hydrochloride; m.p. 86–88° C.

The following example illustrates a method of carrying out the present invention, but it is to be understood that this example is given for purposes of illustration and not of limitation.

EXAMPLE 1

To a solution of 73.25 grams of N,N-bis(3-chloropropyl)methylamine hydrochloride in 100 ml of water is added, with stirring, about 300 ml of ether, followed by a solution of 35.3 grams of sodium carbonate in 300 ml of water. The resulting mixture is agitated vigorously for a period of about 5–10 minutes, the reaction mixture is allowed to stand, and the aqueous and ether layers are separated. The aqueous phase is extracted with 300 ml of ether, and this ether extract is added to the ether layer. The combined ethereal solution is dried over magnesium sulfate, and the ether evaporated therefrom in vacuo at a temperature below 35° C. to give, as a residual oil, the free base, N,N-bis(3-chloropropyl)methylamine.

To this N,N-bis(3-chloropropyl)methylamine is added 166 ml of a 2.06 M solution of trimethylamine in acetonitrile. The resulting mixture is allowed to stand at a temperature of about 25° C. for a period of 21 hours during which time a white solid material crystallizes; the mixture is stirred for an additional 7-hour period, the solid crystalline material is recovered by filtration, washed with a small amount of acetonitrile, then with ether, and finally with hexane, the washings being collected separately. The washed crystalline material is dried in vacuo at 25° C. to give about 6.0 grams of bis(3-trimethylammoniopropyl) methylamine dichloride; the latter is dissolved in isopropanol, an equivalent amount of anhydrous hydrogen chloride is added, and the hydrochloride salt, which precipitates, is recovered by filtration and dried to give substantially pure bis(3-trimethylammoniopropyl)methylamine dichloride hydrochloride; m.p. 251–253° C.

The acetonitrile solution, obtained by filtration of the reaction mixture, is combined with the acetonitrile washings of the diquaternary compound, and the acetonitrile is evaporated from the resulting solution in vacuo at a temperature below about 35° C. The partially crystalline residual material is triturated with 500 ml of ether, the resulting slurry is filtered and the crystals are washed with three portions of ether while minimizing contact of product with air, to give 3-[N-(3-chloropropyl)methylamino]-N,N,N-trimethylpropan-1-aminium chloride, as a crystalline solid. Upon evaporation of the combined ether washings, there is obtained unreacted N,N-bis(3-chloropropyl)methylamine, which is reusable for further quaternization reaction with trimethylamine.

The crystalline 3-[N-(3-chloropropyl)methylamino]-N,N,N-trimethyl-propan-1-aminium chloride is dissolved in 100 ml of isopropanol, and about 10 ml of concentrated aqueous hydrochloric acid is added to the solution; the precipitate which forms crystallizes slowly, and the aqueous-isopropanolic mixture is allowed to stand at room temperature for approximately three days, at the end of which time crystallization is substantially completed. The crystalline slurry is filtered, and the crystalline solid is washed with isopropanol, then with ether and finally with hexane, and is dried in vacuo at a temperature of about 60° C. to give about 23 grams of material which, upon recrystallization from 90 ml of isopropanol, gives about 20 grams of substantially pure 3-[N-(3-chloropropyl)methylamino]-N,N,N-trimethylpropan-1-aminium chloride hydrochloride; m.p. 150–155° C.

Various changes and modifications may be made in carrying out the present invention without departing from the spirit and scope thereof. Insofar as these changes and modifications are within the purview of the annexed claims, they are to be considered as part of this invention.

What is claimed is:

1. The process which comprises reacting together approximately equimolar quantities of N,N-bis(3-chloropropyl)methylamine and trimethylamine, said reaction being conducted in the presence of a polar organic solvent under conditions of time and temperature such that monoquaternization is substantially complete and diquaternization is minimized, thereby forming 3-[N-(3-chloropropyl) methylamine]-N,N,N-trimethyl-propan-1-aminium chloride.

2. The process, as defined in claim 1, in which the reaction is carried out in acetonitrile solution; the by-product bis(3-trimethylammoniopropyl)methylamine dichloride, which crystallizes, is separated from the acetonitrile reaction mixture; acetonitrile is evaporated from the residual solution; and the crystalline material which precipitates is triturated with ether and recovered to give 3-[N-(3-chloropropyl) methylamino]-N,N,N-trimethyl-propan-1-aminium chloride.

3. The process, as defined in claim 1, which comprises reacting N,N-bis(3-chloropropyl)methylamine hydrochloride with a base to form N,N-bis(3-chloropropyl)methylamine; reacting the latter in acetonitrile solution for 20 hours at 25° C. with an equimolar quantity of trimethylamine to form a reaction mixture containing about one part of bis(3-trimethylammoniopropyl)methylamine dichloride and about three parts of 3-[N-(3-chloropropyl)methylamino]-N,N,N-trimethyl-propan-1-aminium chloride; separating the bis(3-trimethylammoniopropyl)-methylamine dichloride, which crystallizes, from the acetonitrile reaction mixture; evaporating the resulting acetonitrile solution, triturating with ether and recovering the residual crystalline 3-[N-(3-chloropropyl)methylamino]-N,N,N-trimethyl-propan-1-aminium chloride; and reacting this crystalline 3-[N-(3-chloropropyl) methylamino]-N,N,N-trimethyl-propan-1-aminium chloride with aqueous isopropanolic hydrochloric acid thereby forming 3-[N-(3-chloropropyl)methylamino]-N,N,N-trimethyl-propan-1-aminium chloride hydrochloride.

* * * * *